United States Patent
Tenten et al.

(10) Patent No.: US 6,740,779 B1
(45) Date of Patent: May 25, 2004

(54) METHOD FOR CARRYING OUT THE CATALYTIC GAS PHASE OXIDATION OF PROPENE TO FORM ACRYLIC ACID

(75) Inventors: Andreas Tenten, Maikammer (DE); Hartmut Hibst, Schriesheim (DE); Otto Machhammer, Mannheim (DE); Claus Hechler, Ludwigshafen (DE); Klaus Joachim Müller-Engel, Stutensee (DE); Signe Unverricht, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/110,227
(22) PCT Filed: Oct. 31, 2000
(86) PCT No.: PCT/EP00/10771
§ 371 (c)(1), (2), (4) Date: Apr. 22, 2002
(87) PCT Pub. No.: WO01/36364
PCT Pub. Date: May 25, 2001

(30) Foreign Application Priority Data

Nov. 16, 1999 (DE) ......... 199 55 168

(51) Int. Cl.$^7$ ............... C07C 57/02
(52) U.S. Cl. ............... 562/598
(58) Field of Search ............... 562/512, 523, 562/542, 544, 545, 546, 547

(56) References Cited

FOREIGN PATENT DOCUMENTS

| DE | 25 13 405 | 10/1976 |
|----|-----------|---------|
| EP | 0 293 224 | 11/1988 |
| EP | 0 900 774 | 3/1999 |
| WO | 00 53558 | 9/2000 |

*Primary Examiner*—Shailendra Kumar
*Assistant Examiner*—Karl Puttlitz
(74) *Attorney, Agent, or Firm*—Oblon, Spivak, McClelland, Maier & Neustadt, P.C.

(57) ABSTRACT

In a process for the two-stage catalytic gas-phase oxidation of propene to acrylic acid, the reaction gas starting mixture is passed, in a tube-bundle reactor, with a propene loading of $\geq 160$ l (S.T.P.) of propene/l·h, first over a fixed catalyst bed 1 present in two successive temperature zones A, B and then over a fixed catalyst bed 2 which is housed either in one further temperature zone C or in two further temperature zones D, E, the temperature of the zone A being kept at a lower temperature than the zone B and the temperature of the zone D at a lower temperature than the zone E.

18 Claims, No Drawings

METHOD FOR CARRYING OUT THE CATALYTIC GAS PHASE OXIDATION OF PROPENE TO FORM ACRYLIC ACID

The present invention relates to a process for the catalytic gas-phase oxidation of propene to acrylic acid, in which a reaction gas starting mixture which comprises propene, molecular oxygen and at least one inert gas and contains the molecular oxygen and the propene in a molar $O_2 : C_3H_6$ ratio of $\geq 1$ is passed, in a first reaction stage, using a propene loading of $\geq 160$ l (S.T.P.) of propene/l of fixed catalyst bed 1 per h, over a fixed catalyst bed 1 which is arranged in two spatially successive reaction zones A, B, the temperature of the reaction zone A being from 300 to 370° C. and the temperature of the reaction zone B being from 305 to 380° C. and simultaneously at least 5° C. above the temperature of the reaction zone A and the active material of which being at least one multimetal oxide containing at least the elements Mo, Fe and Bi, in such a way that the reaction zone A extends to a propene conversion of from 40 to 80 mol % and the propene conversion during a single pass through the fixed catalyst bed 1 is $\geq 90$ mol % and the associated selectivity of the acrolein formation and of the acrylic acid byproduct formation together are $\geq 90$ mol %, and the resulting product gas mixture, which contains the molecular oxygen and the acrolein in a molar $O_2 : C_3H_4O$ ratio of $\geq 0.5$, is passed, in a second reaction stage, over a fixed catalyst bed 2 which is arranged either in a single reaction zone C or in two spatially successive reaction zones D, E, the temperature of the reaction zone C being from 230 to 300° C. and the temperature of the reaction zone D being from 230 to 280° C. and the temperature of the reaction zone E being from 250 to 300° C. and simultaneously at least 5° C. above the temperature of the reaction zone D and the active material of which being at least one multimetal oxide containing at least the elements Mo and V, in such a way that the acrolein conversion during a single pass through the reaction zone C or the reaction zones D and E is $\geq 90$ mol % and the selectivity of the acrylic acid formation balanced over all reaction zones and based on propene converted is $\geq 80$ mol %, the sequence in which the reaction gas starting mixture flows through the reaction zones corresponding to the alphabetic sequence of the reaction zones.

Acrylic acid is a key monomer which is used as such or in the form of its alkyl esters for producing, for example, polymers suitable as adhesives.

The preparation of acrylic acid can be carried out, for example, by two-stage catalytic gas-phase oxidation of propene to acrylic acid.

The process for the two-stage catalytic gas-phase oxidation of propene to acrylic acid is generally known (cf. for example DE-A 3002829). In particular the two reaction stages are known per se (cf. for example EP-A 714700, EP-A 700893, EP-A 15565, DE-C 2830765, DE-C 3338380, JP-A 91/294239, EP-A 807465, WO 98/24746, EP-B 279374, DE-C 2513405, DE-A 3300044, EP-A 575897 and DE-A 19855913).

In particular, it has been proposed to realize the two reaction stages in two tube-bundle reactors which have a plurality of catalyst tubes and each of which has two temperature zones (cf. for example DE-A 19948241, DE-A 19948523, DE-A 19910506, DE-A 19910508 and DE-A 19948248), which is considered advantageous particularly in the case of high loading with starting materials.

In all abovementioned cases, it is advisable to use, for each reaction stage, one tube-bundle reactor comprising a plurality of catalyst tubes, i.e. to carry out the process as a whole in two tube-bundle reactors spatially separated from one another and arranged one behind the other.

The background of this recommendation is the fact that, for example, U.S. Pat. No. 4,029,636 discloses that $MoO_3$ volatilizes from the multimetal oxide catalyst of the first reaction stage operated at the higher temperature and is partially deposited again in the fixed catalyst bed 2 of the second reaction stage having the lower operating temperature.

Consequently, an increase in pressure drop of the reaction gas mixture flowing through the two fixed catalyst beds occurs over time (fixed catalyst bed 2 slowly becomes blocked).

According to EP-A 614 872, the pressure drop established over time is even further increased by the fact that organic materials, for example solid carbon, are additionally regularly deposited in the fixed catalyst bed 2.

According to U.S. Pat. No. 4,029,639, the problem described can be remedied when the two reaction stages are realized in two spatially separated tube-bundle reactors arranged one behind the other and the major part of the abovementioned deposit is effected in an intermediate condenser which is mounted between the two tube-bundle reactors and is equipped with inert solids.

For example, DE-A 2830765 and EP-A 911313 recommend carrying out two-stage catalytic gas-phase oxidation of propene to acrylic acid in a single tube-bundle reactor. However, the propene loading of the fixed catalyst bed 1 in all exemplary embodiments is $\geq 100$ l (S.T.P.) of propene/l of fixed catalyst bed 1 per h. Lower propene loadings are however equivalent to lower $MoO_3$ volatilization since, for example, the amount of water of reaction formed within a specific period (assuming comparable conversions) at lower loading is smaller than at high loading. However, U.S. Pat. No. 4,029,636 discloses that the $MoO_3$ volatilization is promoted in particular by steam.

On the other hand, at a higher propene loading per hour, a larger amount of $MoO_3$ can volatilize since of course a larger saturation amount of $MoO_3$ corresponds to a larger amount of gas.

On the other hand, realizing the two-stage catalytic gas-phase fixed-bed oxidation of propene for the preparation of acrylic acid in two spatially separated tube-bundle reactors comprising a plurality of catalyst tubes entails particularly high capital costs.

It is an object of the present invention to provide a process for the two-stage catalytic gas-phase fixed-bed oxidation of propene to acrylic acid in a single tube-bundle reactor comprising a plurality of catalyst tubes, and to do so with a high propene loading of the fixed catalyst bed 1, which process has the advantage of a pressure drop rapidly increasing over time along the catalyst tubes only in reduced form.

We have found, surprisingly, that this object is achieved if the first reaction stage is realized, as described at the outset, in two spatially successive temperature zones A, B.

The present invention therefore relates to a process for the catalytic gas-phase oxidation of propene to acrylic acid, in which a reaction gas starting mixture which comprises propene, molecular oxygen and at least one inert gas and contains the molecular oxygen and the propene in a molar $O_2 : C_3H_6$ ratio of $\geq 1$ is passed, in a first reaction stage, using a propene loading of $\geq 160$ l (S.T.P.) of propene/l of fixed catalyst bed 1 per h, over a fixed catalyst bed 1 which is arranged in two spatially successive reaction zones A, B, the temperature of the reaction zone A being from 300 to 370° C. and the temperature of the reaction zone B being from 305 to 380° C. and simultaneously at least 5° C. above the temperature of the reaction zone A and the active material of which being at least one multimetal oxide containing at least the elements Mo, Fe and Bi, in such a way that the reaction zone A extends to a propene conversion of from 40 to 80 mol % and the propene conversion during a single pass through the fixed catalyst bed 1 is ≧90 mol % and the associated selectivity of the acrolein formation and of the acrylic acid byproduct formation (overall selectivity of formation of desired product) together are ≧90 mol %, and the resulting product gas mixture, which contains the molecular oxygen and the acrolein in a molar $O_2$: $C_3H_4O$ ratio of ≧0.5, is passed, in a second reaction stage, over a fixed catalyst bed 2 which is arranged either in a single reaction zone C or in two spatially successive reaction zones D, E, the temperature of the reaction zone C being from 230 to 300° C. and the temperature of the reaction zone D being from 230 to 280° C. and the temperature of the reaction zone E being from 250 to 300° C. and simultaneously at least 5° C. above the temperature of the reaction zone D and the active material of which being at least one multimetal oxide containing at least the elements Mo and V, in such a way that the acrolein conversion during a single pass through the reaction zone C or the reaction zones D and E is ≧90 mol % and the selectivity of the acrylic acid formation balanced over all reaction zones and based on propene converted is ≧80 mol %, the sequence in which the reaction gas starting mixture flows through the reaction zones corresponding to the alphabetic sequence of the reaction zones, wherein both reaction stages, i.e. both the fixed catalyst beds 1 and 2 and the reaction zones A, B and C or A, B, D and E, are present in a single tube-bundle reactor comprising a plurality of catalyst tubes.

The temperature of a reaction zone is understood here as meaning the temperature of the fixed catalyst bed fraction present in the reaction zone when the novel process is carried out in the absence of a chemical reaction.

The loading of a catalyst bed with reactant is understood here very generally as meaning the amount of reactant in liters under standard conditions (=l (S.T.P.); the volume in liters which the corresponding amount of reactant would occupy under standard temperature and pressure conditions, i.e. at 25° C. and 1 bar) which is passed as a component of the reaction gas starting mixture per hour through one liter of catalyst bed.

It is preferable according to the invention if the reaction zone A extends to a propene conversion of from 50 to 70, particularly preferably from 65 to 75, mol %.

According to the invention, the temperature of the reaction zone B is advantageously from 310 to 370° C., particularly advantageously from 320 to 370° C.

Furthermore, the temperature of the reaction zone B is preferably at least 10° C. above the temperature of the reaction zone A.

The higher the chosen propene loading of the fixed catalyst bed 1 in the novel process, the greater should be the chosen difference between the temperature of the reaction zone A and the temperature of the reaction zone B. Usually, however, the abovementioned temperature difference in the novel process is not more than 50° C., i.e. the difference between the temperature of the reaction zone A and the temperature of the reaction zone B may be, according to the invention, up to 20° C., up to 25° C., up to 30° C., up to 40° C., up to 45° C. or up to 50° C.

As a rule, the propene conversion in the novel process is ≧92 mol % or ≧94 mol %, based on a single pass through the first reaction stage. With suitable catalyst choice in a manner known per se, the selectivity of formation of the desired product is usually ≧92 mol % or ≧94 mol %, frequently ≧95 mol % or ≧96 mol % or ≧97 mol %.

Surprisingly, the abovementioned applies according to the invention not only in the case of propene loadings of the fixed catalyst bed 1 of ≧165 l (S.T.P.)/l·h or of ≧170 l (S.T.P.)/l·h or ≧175 l (S.T.P.)/l·h or ≧180 l (S.T.P.)/l·h, but also in the case of propene loadings of the fixed catalyst bed 1 of ≧185 l (S.T.P.)/l·h or ≧190 l (S.T.P.)/l·h or ≧200 l (S.T.P.)/l·h or ≧210 l (S.T.P.)/l·h and in the case of loadings ≧220 l (S.T.P.)/l·h or ≧230 l (S.T.P.)/l·h, or ≧240 l (S.T.P.)/l·h or ≧250 l (S.T.P.)/l·h.

It is surprising that the abovementioned values can be reached even when the inert gas used according to the invention comprises ≧30% by volume or ≧40% by volume or ≧250% by volume or ≧60% by volume or ≧70% by volume or ≧80% by volume or ≧290% by volume or ≧95% by volume of molecular nitrogen. In the case of propene loadings above 250 l (S.T.P.)/l·h, the presence of inert (inert diluent gases should in general be those which undergo less than 5%, preferably less than 2%, conversion during a single pass) diluent gases, such as propane, ethane, methane, pentane, butane, $CO_2$, CO, steam and/or noble gases is recommended for the novel process. Of course, these gases and their mixtures can however be present even at lower loadings or can be used as sole diluent gases. It is furthermore surprising that the novel process can be carried out using a fixed catalyst bed 1 which, considered over the reaction zones A, B, is homogeneous, i.e. chemically uniform, without significantly suffering from reduced conversion and/or reduced selectivity.

Usually, the propene loading of the fixed catalyst bed 1 in the novel process will not exceed 600 l (S.T.P.)/l·h. Typically, the propene loadings of the fixed catalyst bed 1 in the novel process are ≦300 l (S.T.P.)/l·h, frequently ≦250 l (S.T.P.)/l·h, without significant reduction in conversion and selectivity.

In the novel process, the operating pressure may be either below atmospheric pressure (e.g. down to 0.5 bar) or above atmospheric pressure. Typically, the operating pressure is from 1 to 5, frequently from 1.5 to 3.5, bar. Usually, the reaction pressure does not exceed 100 bar.

According to the invention, the molar $O_2$:$C_3H_6$ ratio in the reaction gas starting mixture must be ≧1. Usually, this ratio is ≦3. According to the invention, the molar $O_2$:$C_3E_6$ ratio in the reaction starting mixture is frequently ≧1.5 and ≦2.0.

A suitable source of the molecular oxygen required in the novel process is either air or air depleted with respect to molecular nitrogen (e.g. ≧90% by volume of $O_2$, ≦10% by volume of $N_2$).

According to the invention, the propene fraction in the reaction gas starting mixture may be, for example, from 4 to 15, frequently from 5 to 12, % by volume or from 5 to 8% by volume (based in each case on the total volume).

Frequently, the novel process is carried out at a volume ratio of propene to oxygen to inert gases (including steam) in the reaction gas starting mixture of 1:(1.0 to 3.0):(5 to 25), preferably 1:(1.7 to 2.3):(10 to 15).

Usually, the reaction gas starting mixture contains essentially no further components apart from said constituents.

Suitable fixed-bed catalysts 1 for the novel process are all those whose active material is at least one Mo—, Bi— and Fe-containing multimetal oxide.

In other words, it is possible in principle to use, according to the invention, all those catalysts which are disclosed in DE-C 3338380, DE-A 19902562, EP-A 15565, DE-C 2830765, EP-A 807465, EP-A 279374, DE-A 3300044, EP-A 575897, U.S. Pat. No. 4,438,217, DE-A 19855913, WO 98/24746, DE-A 19746210 (those of the formula II), JP-A 91/294239, EP-A 293224 and EP-A 700714. This applies in particular to the exemplary embodiments in these publications, of which those of EP-A 15565, EP-A 575897, DE-A 19746210 and DE-A 19855913 are particularly preferred. Particularly noteworthy in this context are a catalyst according to Example 1c of EP-A 15565 and a catalyst that has to be prepared in a corresponding manner but whose active material has the composition $Mo_{12}Ni_{6.5}Zn_2Fe_2Bi_1P_{0.0065}K_{0.06}O_x \cdot 10SiO_2$. Also noteworthy are the example with the consecutive number 3 in DE-A 19855913 (stoichiometry: $Mo_{12}Co_7Fe_3Bi_{0.6}K_{0.08}Si_{1.6}O_x$) as unsupported catalyst in the form of a hollow cylinder measuring 5 mm×3 mm×2 mm (external diameter×height× internal diameter) and the unsupported catalyst comprising multimetal oxide II and according to Example 1 of DE-A 19746210. The multimetal oxide catalysts of U.S. Pat. No. 4,438,217 may furthermore be mentioned. The latter applies in particular when these hollow cylinders measure 5 mm×2 mm×2 mm, or 5 mm×3 mm×2 mm, or 6 mm×3 mm×3 mm, or 7 mm×3 mm×4 mm (in each case external diameter× height×internal diameter).

A large number of the multimetal oxide active materials suitable according to the invention for the fixed catalyst bed 1 can be subsumed under the formula I

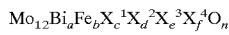  (I), where

X$^1$ is nickel and/or cobalt,

X$^2$ is thallium, an alkali metal and/or an alkaline earth metal,

X$^3$ is zinc, phosphorus, arsenic, boron, antimony, tin, cerium, lead and/or tungsten, X$^4$ is silicon, aluminum, titanium and/or zirconium, a is from 0.5 to 5, b is from 0.01 to 5, preferably from 2 to 4, c is from 0 to 10, preferably from 3 to 10, d is from 0 to 2, preferably from 0.02 to 2, e is from 0 to 8, preferably from 0 to 5, f is from 0 to 10 and n is a number which is determined by the valency and frequency of the elements other than oxygen in I.

They are obtainable in a manner known per se (cf. for example DE-A 4023239) and are usually shaped as such in spheres, rings or cylinders or used in the form of coated catalysts, i.e. premolded, inert supports coated with active material. However, they can of course also be used in powder form as catalysts. According to the invention, the Bi—, Mo— and Fe-comprising multimetal oxide catalyst ACS-4 from Nippon Shokubai can of course also be used.

In principle, the active materials suitable according to the invention for the fixed catalyst bed 1, in particular those of the formula I, can be prepared in a simple manner by producing, from suitable sources of their elemental constituents, a very intimate, preferably finely divided dry blend having a composition corresponding to their stoichiometry and calcining said dry blend at from 350 to 650° C. The calcination can be carried out both under inert gas and under an oxidizing atmosphere, e.g. air (mixture of inert gas and oxygen) and also under a reducing atmosphere (e.g. mixture of inert gas, NH$_3$, CO and/or H$_2$). The duration of calcination may be from a few minutes to a few hours and usually decreases with increasing temperature. Suitable sources of the elemental constituents of the multimetal oxide active materials I are those compounds which are already oxides and/or those compounds which can be converted into oxides by heating, at least in the presence of oxygen.

In addition to the oxides, suitable such starting compounds are in particular halides, nitrates, formates, oxalates, citrates, acetates, carbonates, amine complexes, ammonium salts and/or hydroxides (compounds such as NH$_4$OH, (NH$_4$)$_2$CO$_3$, NH$_4$NO$_3$, NH$_4$CHO$_2$, CH$_3$COOH, NH$_4$CH$_3$CO$_2$ and/or ammonium oxalate, which are decomposed and/or can be decomposed at the latest during the subsequent calcination to give compounds escaping in gaseous form, may additionally be incorporated into the intimate dry blend).

The thorough mixing of the starting compounds for the preparation of multimetal oxide materials I can be carried out in dry or in wet form. If it is effected in dry form, the starting compounds are expediently used in the form of finely divided powders and, after mixing and any compaction, are subjected to the calcination. However, the thorough mixing is preferably effected in wet form. Usually, the starting compounds are mixed with one another in the form of an aqueous solution and/or suspension. Particularly intimate dry blends are obtained in the mixing method described when exclusively sources of the elemental constituents in dissolved form are used as starting materials. The preferably used solvent is water. The aqueous material obtained is then dried, the drying process preferably being carried out by spray-drying the aqueous mixture with outlet temperatures of from 100 to 150° C.

The multimetal oxide materials suitable according to the invention as active material for the fixed-bed catalysts 1, in particular those of the formula I, can be used for the novel process both in powder form and after shaping to give specific catalyst geometries, it being possible to effect the shaping before or after the final calcination. For example, unsupported catalysts can be prepared from the powder form of the active material or its uncalcined and/or partially calcined precursor material by compaction to give the desired catalyst geometry (for example by pelleting or extrusion), it being possible, if required, to add assistants, e.g. graphite or stearic acid as lubricants and/or molding assistants and reinforcing agents, such as microfibers of glass, asbestos, silicon carbide or potassium titanate. Suitable geometries for unsupported catalysts are, for example, solid cylinders or hollow cylinders having an external diameter and a length of from 2 to 10 mm. In the case of the hollow cylinders, a wall thickness of 1 to 3 mm is expedient. Of course, the unsupported catalyst can also have spherical geometry, where the sphere diameter can be from 2 to 10 mm.

The shaping of the pulverulent active material or its pulverulent, still uncalcined and/or partially calcined precursor material can of course also be effected by application to premolded inert catalyst supports. The coating of the supports for the preparation of the coated catalysts is carried out as a rule in a suitable rotatable container, as disclosed, for example, in DE-A 2909671, EP-A 293859 or EP-A 714700. Expediently, for coating the supports, the powder material to be applied is moistened and, after application, is dried again, for example by means of hot air. The coat thickness of the powder material applied to the support is expediently chosen to be in the range from 10 to 1000 µm, preferably from 50 to 500 µm, particularly preferably from 150 to 250 µm.

Conventional porous or nonporous aluminas, silica, thorium dioxide, zirconium dioxide, silicon carbide or silicates, such as magnesium silicate or aluminum silicate can be used as support materials. The supports may have a regular or irregular shape, those having a regular shape and substantial surface roughness, e.g. spheres or hollow cylinders, being preferred. The use of essentially nonporous, spherical steatite supports which have a rough surface and whose diameter is from 1 to 8 mm, preferably from 4 to 5 mm, is suitable. However, the use of cylinders whose length is from 2 to 10 mm and whose external diameter is from 4 to 10 mm as supports is also suitable. When rings suitable according to the invention are used as supports, the wall thickness is moreover usually from 1 to 4 mm. Annular supports preferably to be used according to the invention have a length of from 2 to 6 mm, an external diameter of from 4 to 8 mm and a wall thickness of from 1 to 2 mm. Rings measuring 7 mm×3 mm×4 mm (external diameter×length×internal diameter) are also particularly suitable according to the invention as supports. The fineness of the catalytically active oxide materials to be applied to the surface of the support is of course adapted to the desired coat thickness (cf. EP-A 714 700).

Advantageous multimetal oxide active materials to be used according to the invention for the fixed catalyst bed 1 are furthermore materials of the formula II

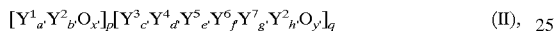

$$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \quad (II),$$

where $Y^1$ is bismuth, tellurium, antimony, tin and/or copper, $Y^2$ is molybdenum and/or tungsten, $Y^3$ is an alkali metal, thallium and/or samarium, $Y^4$ is an alkaline earth metal, nickel, cobalt, copper, manganese, zinc, tin, cadmium and/or mercury, $Y^5$ is iron, chromium, cerium and/or vanadium, $Y^6$ is phosphorus, arsenic, boron and/or antimony, $Y^7$ is a rare earth metal, titanium, zirconium, niobium, tantalum, rhenium, ruthenium, rhodium, silver, gold, aluminum, gallium, indium, silicon, germanium, lead, thorium and/or uranium, a' is from 0.01 to 8, b' is from 0.1 to 30, c' is from 0 to 4, d' is from 0 to 20, e' is from 0 to 20, f' is from 0 to 6, g' is from 0 to 15, h' is from 8 to 16, x' and y' are numbers which are determined by the valency and frequency of the elements other than oxygen in II, and p and q are numbers whose ratio p/q is from 0.1 to 10, containing three-dimensional regions of the chemical composition $Y^1_{a'}Y^2_{b'}O_{x'}$, which are delimited from their local environment owing to their composition differing from their local environment and whose largest diameter (longest line passing through the center of gravity of the region and connecting two points present on the surface (interface) of the region) is from 1 nm to 100 μm, frequently from 10 nm to 500 nm or from 1 μm to 50 or 25 μm.

Particularly advantageous novel multimetal oxide materials II are those in which $Y^1$ is bismuth.

Preferred among these in turn are those of the formula III $$[Bi_{a''}Z^2_{b''}O_{x''}]_{p''}[Z^2_{12}Z^3_{c''}Z^4_{d''}Fe_{e''}Z^5_{f''}Z^6_{g''}Z^7_{h''}O_{y''}]_{q''} \quad (III)$$

where $Z^2$ is molybdenum and/or tungsten, $Z^3$ is nickel and/or cobalt, $Z^4$ is thallium, an alkali metal and/or an alkaline earth metal, $Z^5$ is phosphorus, arsenic, boron, antimony, tin, cerium and/or lead, $Z^6$ is silicon, aluminum, titanium and/or zirconium, $Z^7$ is copper, silver and/or gold, a" is from 0.1 to 1, b" is from 0.2 to 2, c" is from 3 to 10, d" is from 0.02 to 2, e" is from 0.01 to 5, preferably from 0.1 to 3, f" is from 0 to 5, g" is from 0 to 10, h" is from 0 to 1, x" and y" are numbers which are determined by the valency and frequency of the elements other than oxygen in III, and p" and q" are numbers whose ratio p"/q" is from 0.1 to 5, preferably from 0.5 to 2, those materials III in which $Z^2_{b''}$ is (tungsten)$_{b''}$ and $Z^2_{12}$ is (molybdenum)$_{12}$ being very particularly preferred.

It is also advantageous if at least 25 mol % (preferably at least 50, particularly preferably at least 100, mol %) of the total amount $[Y^1_{a'}Y^2_{b'}O_{x'}]_p([Bi_{a''}Z^2_{b''}O_{x''}]_{p''})$ of the multimetal oxide materials II (multimetal oxide materials III) suitable according to the invention are present in the multimetal oxide materials II (multimetal oxide materials III) suitable according to the invention in the form of three-dimensional regions of the chemical composition $Y^1_{a'}Y^2_{b'}O_{x'}[Bi_{a''}Z^2_{b''}O_{x''}]$ which are delimited from their local environment owing to their chemical composition differing from their local environment and whose largest diameter is from 1 nm to 100 μm.

Regarding the shaping, the statements made in the case of the catalysts comprising multimetal oxide materials I are applicable with respect to catalysts comprising the multimetal oxide materials II.

In contrast to the fixed catalyst bed 1, according to the invention the fixed catalyst bed 2 may be present either in one reaction zone having a uniform temperature (reaction zone C) or in two spatially successive reaction zones D, E having temperatures differing from one another.

It is expedient according to the invention if the temperature of the reaction zone C is from 230 to 285° C. Furthermore according to the invention, the temperature of the reaction zone D is expediently from 245 to 275° C. and, according to the invention, the temperature of the reaction zone E is advantageously at least 20° C. above the temperature of the reaction zone D and is advantageously from 265 to 295° C.

The higher the chosen propene loading of the fixed catalyst bed 1, and hence entirely automatically the acrolein loading of the fixed catalyst bed 2, in the novel process, the more advantageous is the use of two temperature zones D, E instead of one temperature zone C. The difference between the temperature of the reaction zone D and the temperature of the reaction zone E should be chosen to be the greater the higher the chosen reactant loading.

However, the abovementioned temperature difference in the novel process is usually not more than 40° C., i.e. the difference between the temperature of the reaction zone D and the temperature of the reaction zone E may be, accord-

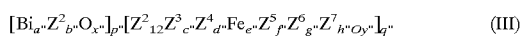

ing to the invention, up to 15° C., up to 25° C., up to 30° C., up to 35° C. or up to 40° C.

It is important according to the invention that the oxygen required in the second reaction stage is already present in the reaction gas starting mixture for the first reaction stage.

Apart from the constituents stated in this publication, the reaction gas starting mixture usually contains essentially no further components.

The acrolein loading of the fixed catalyst bed 2 in the novel process is an automatic consequence of the propene loading chosen in the first reaction stage for the fixed catalyst bed 1 and the reaction conditions chosen in the first reaction stage, including the chosen composition of the reaction gas starting mixture.

In the novel process, the acrolein loading of the fixed catalyst bed 2 is as a rule about 10 l (S.T.P.)/l·h, frequently about 20 or 25 l (S.T.P.)/l·h, below the propene loading of the fixed catalyst bed 1. This is primarily due to the fact that, in the first reaction stage, both conversion and selectivity with respect to acrolein generally do not reach 100%.

When the fixed catalyst bed 2 is chosen in a suitable manner known per se, in the novel process the selectivity of the acrylic acid formation, balanced over both reaction stages and based on propene converted, may be ≧83 mol %, frequently ≧85 mol % or ≧88 mol %, often ≧90 mol % or ≧93 mol %, even in the case of very high propene loadings of fixed catalyst bed 1.

Suitable fixed-bed catalysts 2 to be used according to the invention in the gas-phase catalytic acrolein oxidation in the second reaction stage are all those whose active material is at least one Mo— and V-containing multimetal oxide.

Suitable multimetal oxide active materials of this type are described, for example, in U.S. Pat. No. 3,775,474, U.S. Pat. No. 3,954,855, U.S. Pat. No. 3,893,951 and U.S. Pat. No. 4,339,355. Also particularly suitable are the multimetal oxide active materials of EP-A 427 508, of DE-A 2 909 671, of DE-C 31 51 805, of German Published Application DAS 2 626 887, of DE-A 43 02 991, of EP-A 700 893, of EP-A 714 700 and of DE-A 19 73 6105. Particularly preferred in this context are the exemplary embodiments of EP-A 714 700 and of DE-A 19 73 6105.

A large number of the multimetal oxide active materials suitable for fixed-bed catalysts 2 can be subsumed under the formula IV

where

X$^1$ is W, Nb, Ta, Cr and/or Ce,
X$^2$ is Cu, Ni, Co, Fe, Mn and/or Zn,
X$^3$ is Sb and/or Bi,
X$^4$ is one or more alkali metals,
X$^5$ is one or more alkaline earth metals,
X$^6$ is Si, Al, Ti and/or Zr,
a is from 1 to 6,
b is from 0.2 to 4,
c is from 0.5 to 18,
d is from 0 to 40,
e is from 0 to 2,
f is from 0 to 4,
g is from 0 to 40 and
n is a number which is determined by the valency and frequency of the elements other than oxygen in IV.

Preferred embodiments within the active multimetal oxides IV are those which are covered by the following meanings of the variables of the formula IV:

X$^1$ is W, Nb, and/or Cr,
X$^2$ is Cu, Ni, Co, and/or Fe,
X$^3$ is Sb,
X$^4$ is Na and/or K,
X$^5$ is Ca, Sr and/or Ba,
X$^6$ is Si, Al, and/or Ti,
a is from 1.5 to 5,
b is from 0.5 to 2,
c is from 0.5 to 3,
d is from 0 to 2,
e is from 0 to 0.2,
f is from 0 to 1 and
n is a number which is determined by the valency and frequency of the elements other than oxygen in IV.

However, very particularly preferred multimetal oxides IV are those of the formula V

where

Y$^1$ is W and/or Nb,
Y$^2$ is Cu and/or Ni,
Y$^5$ is Ca and/or Sr,
Y$^6$ is Si and/or Al,
a' is from 2 to 4,
b' is from 1 to 1.5,
c' is from 1 to 3,
f' is from 0 to 0.5,
g' is from 0 to 8 and
n' is a number which is determined by the valency and frequency of the elements other than oxygen in V.

The multimetal oxide active materials (IV) suitable according to the invention are obtainable in a manner known per se, for example disclosed in DE-A 4335973 or in EP-A 714700.

In principle, multimetal oxide active materials suitable according to the invention for fixed-bed catalysts 2, in particular those of the formula IV, can be prepared in a simple manner by producing, from suitable sources of their elemental constituents, a very intimate, preferably finely divided dry blend having a composition corresponding to their stoichiometry and calcining said dry blend at from 350 to 600° C. The calcination can be carried out both under inert gas and under an oxidizing atmosphere, e.g. air (mixture of inert gas and oxygen) and also under a reducing atmosphere (e.g. mixtures of inert gas and reducing gases, such as H$_2$, NH$_3$, CO, methane and/or acrolein or said reducing gases by themselves). The duration of calcination may be from a few minutes to a few hours and usually decreases with increasing temperature. Suitable sources of the elemental constituents of the multimetal oxide active materials IV are those compounds which are already oxides and/or those compounds which can be converted into oxides by heating, at least in the presence of oxygen.

The thorough mixing of the starting compounds for the preparation of multimetal oxide materials IV can be carried out in dry or in wet form. If it is effected in dry form, the starting compounds are expediently used in the form of finely divided powders and, after the mixing and any compaction, are subjected to the calcination. However, thorough mixing is preferably effected in wet form.

Usually, the starting compounds are mixed with one another in the form of an aqueous solution and/or suspension. Particularly intimate dry blends are obtained in the mixing method described when exclusively dissolved sources of the elemental constituents are used as starting materials. The preferably used solvent is water. The aqueous material obtained is then dried, the drying process preferably being effected by spray-drying the aqueous mixture with outlet temperatures of from 100 to 150° C.

The multimetal oxide materials suitable according to the invention as active materials of the fixed-bed catalyst 2 for the second reaction stage, in particular those of the formula IV, can be used for the novel process both in powder form and shaped to give specific catalyst geometries, it being possible to effect the shaping before or after the final calcination. For example, unsupported catalysts can be prepared from the powder form of the active material or its uncalcined precursor material by compaction to give the desired catalyst geometry (for example by pelleting or extrusion), it being possible, if required, to add assistants, e.g. graphite or stearic acid as lubricants and/or molding assistants and reinforcing agents, such as microfibers of glass, asbestos, silicon carbide or potassium titanate. Suitable geometries for unsupported catalysts are, for example, solid cylinders or hollow cylinders having an external diameter and a length of from 2 to 10 mm. In the case of the hollow cylinders, a wall thickness of from 1 to 3 mm is expedient. The unsupported catalyst can of course also have spherical geometry, where the sphere diameter can be from 2 to 10 mm.

The shaping of the pulverulent active material or its pulverulent, still uncalcined precursor material can of course also be effected by application to premolded inert catalyst supports. The coating of the supports for the preparation of the coated catalysts is carried out as a rule in a suitable rotatable container, as disclosed, for example, in DE-A 2909671, EP-A 293859 or EP-A 714700.

For coating the supports, the powder material to be applied is expediently moistened and, after application, is dried again, for example by means of hot air. The coat thickness of the powder material applied to the support is expediently chosen to be in the range from 10 to 1000 $\mu$m, preferably from 50 to 500 $\mu$m, particularly preferably from 150 to 250 $\mu$m.

Conventional porous or nonporous aluminas, silica, thorium dioxide, zirconium dioxide, silicon carbide or silicates, such as magnesium silicate or aluminum silicate, can be used as support materials. The supports may have a regular or irregular shape, those having a regular shape and substantial surface roughness, e.g. spheres or hollow cylinders, being preferred. The use of essentially nonporous, spherical steatite supports which have a rough surface and whose diameter is from 1 to 8 mm, preferably from 4 to 5 mm, is suitable. However, the use of cylinders whose length is from 2 to 10 mm and whose external diameter is from 4 to 10 mm as supports is also suitable. When rings suitable according to the invention are used as supports, the wall thickness is moreover usually from 1 to 4 mm. Annular supports preferably to be used according to the invention have a length of from 2 to 6 mm, an external diameter of from 4 to 8 mm and a wall thickness of from 1 to 2 mm. Rings measuring 7 mm×3 mm×4 mm (external diameter×length×internal diameter) are particularly suitable according to the invention as supports. The fineness of the catalytically active oxide materials to be applied to the surface of the support is of course adapted to the desired coat thickness (cf. EP-A 714 700).

Advantageous multimetal oxide active materials to be used according to the invention as fixed-bed catalysts 2 for the second reaction stage are furthermore materials of the formula VI, $$[D]_p[E]_q \tag{VI},$$

where

D is $Mo_{12}V_{a''}Z^1_{b''}Z^2_{c''}Z^3_{d''}Z^4_{e''}Z^5_{f''}Z^6_{g''}O_{x''}$,

E is $Z^7_{12}Cu_{h''}H_{i''}O_{y''}$, $Z^1$ is W, Nb, Ta, Cr and/or Ce, $Z^2$ is Cu, Ni, Co, Fe, Mn and/or Zn, $Z^3$ is Sb and/or Bi, $Z^4$ is Li, Na, K, Rb, Cs and/or H $Z^5$ is Mg, Ca, Sr and/or Ba, $Z^6$ is Si, Al, Ti and/or Zr, $Z^7$ is Mo, W, V, Nb and/or Ta, a" is from 1 to 8, b" is from 0.2 to 5, c" is from 0 to 23, d" is from 0 to 50, e" is from 0 to 2, f" is from 0 to 5, g" is from 0 to 50, h" is from 4 to 30, i" is from 0 to 20 and x",y" are numbers which are determined by the valency and frequency of the elements other than oxygen in VI p and q are numbers which differ from 0 and whose ratio p/q is from 160:1 to 1:1, which are obtainable by separately preforming a multimetal oxide material E $$Z^7_{12}Cu_{h''}H_{i''}O_{y''} \tag{E},$$

in finely divided form (starting material 1) and then incorporating the preformed solid starting material 1 into an aqueous solution, an aqueous suspension or finely divided dry blend of sources of the elements Mo, V, $Z^1$, $Z^2$, $Z^3$, $Z^4$, $Z^5$, $Z^6$, which contains the abovementioned elements in the stoichiometry D $$Mo_{12}V_{a''}Z^1_{b''}Z^2_{c''}Z^3_{d''}Z^4_{e''}Z^5_{f''}Z^6_{g''} \tag{D},$$

(starting material 2), in the desired ratio p:q, drying any resulting aqueous mixture and calcining the resulting dry precursor material at from 250 to 600° C. before or after its drying to give the desired catalyst geometry.

The multimetal oxide materials VI in which the incorporation of the preformed solid starting material 1 into an aqueous starting material 2 is effected at ≧70° C. are preferred. A detailed description of the preparation of catalysts comprising multimetal oxide materials VI is contained, for example, in EP-A 668164, DE-A 19736105 and DE-A 19528646.

Regarding the shaping, the statements made in the case of the catalysts comprising multimetal oxide materials IV are applicable with respect to catalysts comprising multimetal oxide materials VI.

In the novel process, it is of course possible to use both fixed catalyst beds 1 and fixed catalyst beds 2 whose volume-specific activity in the direction of flow of the reaction gas starting mixture increases continuously, abruptly or stepwise (this can be effected, for example, as described in WO 98/24746, EP-A 450596, EP-A 792866 or JP-A 91/294239 or by dilution with inert material). According to the invention, it is also possible, in addition to nitrogen, steam and/or oxides of carbon, to use the inert diluent gases recommended in EP-A 293224 and in EP-B 257565 (e.g. only propane or only methane, etc.). The latter may, if required, also be used in combination with a volume-specific activity of the fixed catalyst beds which increases in the direction of flow of the reaction gas mixture.

According to the invention, the reaction zone B may be present spatially directly next to the reaction zone C or D, i.e. the fixed catalyst beds 1 and 2 may, according to the invention, be directly adjacent to one another. However, they can of course also be separated from one another by inert material beds and/or air.

Suitable separating inert materials are, for example, the inert materials separating reaction zones from one another in DE-C 2830765 and those in EP-A 911313. According to the invention, such an inert material bed is included with the fixed catalyst bed 2, i.e. is kept at the same temperature as the reaction zone C or D.

It is essential to the invention that both reaction stages, i.e. both the fixed catalyst beds 1 and 2 and the reaction zones A, B and C or A, B, D and E are present in a single tube-bundle reactor comprising a plurality of catalyst tubes.

In other words, the novel process must be realized in a tube-bundle reactor having a plurality of temperature zones, as disclosed by the example of two temperature zones in DE-C 2830765, DE-C 2513405, U.S. Pat. No. 3,147,084, DE-A 2201528, EP-A 383224 and DE-A 2903218.

In other words, the fixed catalyst beds 1 and 2 to be used according to the invention and an inert material bed which may separate them from one another are present spatially successively in the metal tubes of a tube-bundle reactor (in the case of a vertical orientation of the reaction tubes, expediently that fixed catalyst bed out of the two fixed catalyst beds whose time-on-screen is the shorter is present at the top) and heating media, as a rule salt melts, which are essentially spatially separated from one another, are passed around the metal tubes. The tube section over which the respective salt bath extends represents, according to the invention, a temperature zone, i.e. in the usual case according to the invention, a salt bath A flows around that section of the tubes (reaction zone A) in which the oxidative conversion of the propene (in a single pass) takes place until a conversion of from 40 to 80 mol % is reached, and a salt bath B flows around that section of the tubes (reaction zone B) in which the subsequent oxidative conversion of the propene (in a single pass) takes place until a conversion of at least 90 mol % is reached. In both abovementioned tube sections, the fixed catalyst bed 1 is present. A further salt bath C or two further salt baths D, E flow around the tube sections within which the fixed catalyst bed 2 and, if required, the inert material bed separating the two fixed catalyst beds from one another are present and in which the acrolein conversion takes place.

Usually, the beginning of the reaction zone B is behind the hot-spot maximum of the reaction zone A. In a corresponding manner, the beginning of the reaction zone E is usually behind the hot-spot maximum of the reaction zone D. As a rule, the reaction zone D extends up to a conversion of the acrolein, which emerges from the first reaction stage, of from 55 to 85 mol %, preferably from 65 to 80 mol %.

Each of the heating (salt) baths A, B, C or A, B, D, E can, according to the invention, be passed cocurrently or countercurrently through the space surrounding the reaction tubes, relative to the direction of flow of the reaction mixture flowing through the reaction tubes.

Expediently, cocurrent or countercurrent flow is used in all reaction zones. It is also advantageous to use cocurrent flow in reaction zone A and countercurrent flow in reaction zone B (or vice versa). The same applies to the reaction zones D, E.

In all abovementioned configurations within the respective reaction zone, it is of course possible also to superpose a transverse flow on the flow of the heating medium parallel to the reaction tubes, so that the individual reaction zone corresponds to a tube-bundle reactor as described in EP-A 700714 or in EP-A 700893 and a meandering flow of the heat exchange medium results overall in the longitudinal section through the catalyst tube bundle.

Expediently, the reaction gas starting mixture is preheated to the reaction temperature before being fed to the fixed catalyst bed 1.

In the abovementioned tube-bundle reactors, the catalyst tubes are usually made of ferritic steel and typically have a wall thickness of from 1 to 3 mm. Their internal diameter is as a rule from 20 to 30 mm, frequently from 21 to 26 mm. It is expedient in terms of application technology if the number of catalyst tubes housed in the tube-bundle container is at least 5000, preferably at least 10,000. Frequently, the number of catalyst tubes housed in the reaction container is from 15,000 to 30,000. Tube-bundle reactors having more than 40,000 catalyst tubes tend to be the exception. Inside the container, the catalyst tubes are usually homogeneously distributed, the distribution expediently being chosen so that the distance between the central inner axes of adjacent catalyst tubes (i.e. the catalyst tube spacing) is from 35 to 45 mm (cf. for example EP-B 468290).

Particularly suitable heat exchange media are fluid thermostating media. The use of melts of salts, such as potassium nitrate, potassium nitrite, sodium nitrite and/or sodium nitrate or of metals having a low melting point, such as sodium, mercury and alloys of various metals, is particularly advantageous.

In all abovementioned configurations of the flow in the multizone tube-bundle reactors, the flow rate within the required circulations of heat exchange media are as a rule chosen so that the temperature of the heat exchange medium increases by from 0 to 15° C. from the point of entry into the reaction zone to the point of exit from the reaction zone (owing to the exothermic nature of the reaction), i.e. the abovementioned $\Delta T$ may be, according to the invention, from 1 to 10° C. or from 2 to 8° C. or from 3 to 6° C.

According to the invention, the temperature of the heat exchange medium on entering the reaction zone A is usually from 300 to 370° C. According to the invention, the temperature of the heat exchange medium on entering the reaction zone B is usually on the one hand from 305 to 380° C. and, on the other hand, simultaneously at least 5° C. above the temperature of the heat exchange medium entering the reaction zone A.

Preferably, the temperature of the heat exchange medium on entering the reaction zone B is at least 10° C. above the temperature of the heat exchange medium entering the reaction zone A. The difference between the temperatures on entering the reaction zones A and B may thus be, according to the invention, up to 10° C., up to 20° C., up to 25° C., up to 30° C., up to 40° C., up to 45° C. or up to 50° C. Usually, however, the abovementioned temperature difference is not more than 50° C. The higher the chosen propene loading of the fixed catalyst bed 1 in the novel process, the greater should be the difference between the temperature of the heat exchange medium on entering the reaction zone A and the temperature of the heat exchange medium on entering reaction zone B.

According to the invention, the temperature of the heat exchange medium on entering the reaction zone B is advantageously from 305 to 375° C., particularly advantageously from 305 to 370° C.

In a corresponding manner, the temperature of the heat exchange medium on entering the reaction zone C is usually from 230 to 300° C., preferably from 230 to 285° C.

The temperature of the heat exchange medium on entering the reaction zone D is usually from 230 to 280° C. (expediently from 245 to 275° C.) and the temperature of the heat exchange medium on entering the reaction zone E is usually from 250 to 300° C. (expediently from 265 to 295° C.).

The temperature of the heat exchange medium on entering the reaction zone E is preferably at least 10° C. or at least 20° C. above the temperature of the heat exchange medium on entering the reaction zone D.

According to the invention, the chosen difference between the temperature of the heat exchange medium on entering the reaction zone E and that on entering the reaction zone D should be the greater the higher the chosen propene loading of the fixed catalyst bed 1. This difference is usually not more than 5° C. However, it may be up to 15° C., up to 25° C., up to 30° C., up to 35° C. or up to 40° C.

If, according to the invention, the fixed catalyst beds 1 and 2 are separated from one another by an inert material bed, the length of the inert material bed is usually ≦30%, frequently ≦20%, but as a rule ≧10% of the length of the fixed catalyst bed 2.

Such inert materials may be, for example, stainless steel coils, steatite rings or steatite beads. However, the inert materials may also be individual coils to be introduced into the reaction tubes and having a length of up to 50 cm (cf. EP-B 351167).

At this point, it should once again be pointed out that, for realizing the novel multizone procedure, it is possible also to apply in particular the principle which is described in German Published Application DAS 2,201,528 and which includes the possibility of transferring a portion of the hotter heat exchange medium of one reaction zone to a colder heat exchange medium of another reaction zone in order, if required, to heat up a cold reaction gas starting mixture or a cold recycled gas.

Furthermore, the tube bundle characteristic within an individual reaction zone may be designed as described in EP-A 382098.

It is noteworthy that, with a predetermined propene loading and predetermined conversion and selectivity, the novel procedure results in a substantially slower increase in the pressure drop in reaction zone C or in reaction zones D, E. This is due, inter alia, to the fact that the novel design of the first reaction stage very evidently reduces the volatilization of the $MoO_3$, which finally actually permits the novel procedure to be carried out in a single tube-bundle reactor.

Another essential feature of the invention is that the novel process does not necessarily require the presence of an intermediate layer of inert material.

The novel process is particularly suitable for a continuous procedure.

The novel process gives not pure acrylic acid but a mixture from whose secondary components the acrylic acid can be isolated in a manner known per se (for example by rectification and/or crystallization). Unconverted acrolein and propene and inert diluent gas used and/or formed in the course of the reaction can be recycled to the gas-phase oxidation. In the novel two-stage gas-phase oxidation starting from propene, the recycling is expediently effected into the reaction zone A.

Otherwise, in this publication, conversion, selectivity and residence time are defined as follows, unless stated otherwise:

$$\text{Conversion of starting material (\%)} = \frac{\text{number of moles of starting material converted}}{\text{number of moles of starting material used}} \times 100$$

$$\text{Selectivity of product formation} = \frac{\text{number of moles of starting material converted into product}}{\text{number of moles of starting material converted}} \times 100$$

$$\text{Residence time (sec.)} = \frac{\text{empty reactor volume filled with catalyst (l)}}{\text{throughput of reaction gas starting mixture } (1(S.T.P.)/h)} \times 3600$$

EXAMPLE AND COMPARATIVE EXAMPLE

1) Preparation of a Fixed-bed Catalyst 1

213 kg of ammonium heptamolybdate were dissolved a little at a time at 60° C. in 600 l of water, and 0.97 kg of a 46.8% strength by weight potassium hydroxide solution at 20° C. was added while stirring. A second solution was prepared by adding 116.25 kg of an iron nitrate solution (14.2% by weight of iron) to 333.7 kg of a cobalt nitrate solution (12.4% by weight of cobalt), the temperature being kept at 30° C. and stirring being continued for a further 30 minutes after the end of the addition. 112.3 kg of a bismuth nitrate solution (11.2% by weight of bismuth) were metered at 60° C. into the iron-cobalt solution. The second solution was added to the molybdate solution within a period of 30 minutes at 60° C. 15 minutes after the end of the addition, 19.16 kg of silica sol (46.80% by weight of $SiO_2$) were added to the slurry obtained. Stirring was then carried out for 15 minutes. The slurry obtained was then spray-dried (gas inlet temperature=310° C., gas outlet temperature=140° C.), a powder having a loss on ignition (3 h at 600° C.) of about 30% by weight being obtained.

The composition of the active material is $Mo_{12}Co_7Fe_{2.94}Bi_{0.6}Si_{1.59}K_{0.08}O_x$.

After the spray-drying, the starting material was mixed with 1.5% by weight of graphite, compacted and molded into cylindrical rings having an external diameter of 5 mm, a height of 3 mm and a hole diameter of 2 mm. The molded rings were calcined under air in a belt calcination apparatus having eight chambers. The chambers were thermostated at 160° C., 200° C., 230° C., 270° C., 380° C., 430° C., 500° C. and once again 500° C. The residence time was 2 hours each in the first to fourth chamber and 5 hours in the fifth to eighth chamber. The catalyst obtained is the fixed-bed catalyst 1.

2) Preparation of a Fixed-bed Catalyst 2 a) Preliminary Preparation of a Phase B Having the Stoichiometry $Cu_{1.0}Mo_{0.5}W_{0.5}O_4$ 620 l of water were initially taken in a first stirred kettle at about 25° C. with stirring. 27.4 kg of $(NH_4)_6Mo_7O_{24} \cdot 4H_2O$ were then added. After heating, 40.4 kg of $(NH_4)_{10}W_{12}O_{41} \cdot 7H_2O$ were added and the mixture was heated to 90° C. with further stirring. A clear yellow-orange solution was obtained (solution 1).

Simultaneously with the preparation of the solution 1, 373 l of water were initially taken in a second stirred kettle at about 25° C. with stirring. 61 l of a 25% strength by weight aqueous $NH_3$ solution were then stirred in. 61.9 kg of copper(II) acetate were added to the ammoniacal solution and the mixture obtained was stirred until a clear, dark blue solution without sediment was obtained (solution 2).

Solution 2 was transferred from the second stirred kettle into the solution 1. The turquoise-colored slurry obtained was then spray-dried, the gas inlet temperature at the spray tower being 250° C. and the gas outlet temperature being 140° C. The spray-drying was carried out by the cocurrent method.

75 kg of the spray-dried powder produced were metered into a kneader and kneaded with addition of 15 l of water. Thereafter, the kneaded material was emptied into an extruder and was molded by means of the extruder to give extrudates (length 1–2 cm; diameter 6 mm).

The extrudates were dried on a belt dryer at 120° C.

The catalyst precursor was calcined in a rotating tube by a continuous procedure at 340° C. and in a residence time of at least 1 hour in an airstream. The precursor was then calcined again at 790° C.

The extrudates were then milled in a mill (Biplex mill BQ 500) to a mean particle diameter of from 3 to 5 μm.

The resulting powder had a BET surface area of $\leq 1$ m$^2$/g. The following phases were detected by means of X-ray diffraction:

1. $CuMoO_4$-III having a wolframite structure,
2. HT copper molybdate.

b) Preliminary Preparation of a Precursor Material for the Phase A having the Stoichiometry $Mo_{10.4}V_3W_{1.2}O_x$ 900 l of water were initially taken in a stirred kettle at about 25° C. with stirring (70 rpm). Thereafter, 122.4 kg of $(NH_4)_6Mo_7O_{24} \cdot H_2O$ were added and the mixture was heated to 90° C. with stirring. 22.2 kg of $NH_4VO_3$ (ammonium metavanadate) were then added. 20.9 kg of $(NH_4)_{10}W_{12}O_{41} \cdot 7H_2O$ were then added; stirring for 60 minutes at 90° C. gave a clear orange solution. Its pH was 6.2±0.3. The pH was initially reduced to 5.0±0.3 by adding acetic acid and then increased again to 6.2±0.3 by stirring in 25% strength by weight aqueous $NH_3$ solution. In the end, a clear, orange solution without sediment was obtained. This was then spray-dried, the gas inlet temperature of the spray tower being 240° C. and the gas outlet temperature being 100° C. The spray-dried powder obtained was light yellow.

c) Preparation of the Multimetal Oxide Active Material 75 kg of the spray-dried powder obtained under b) were initially taken in a trough kneader having two Z-shaped, horizontally mounted kneading arms. Thereafter, 8.6 l of acetic acid were added and then a kneadable consistency was established by adding the required amount of water. 12.9 kg of the previously prepared phase B were then added and kneading was carried out until homogeneity was obtained. Thereafter, the kneaded material was emptied into an extruder and was molded by means of the extruder to give extrudates (length 1–2 cm; diameter 6 mm). The extrudates were dried on a belt dryer at 120° C.

300 kg of the moldings thus produced were loaded onto a tray cart equipped with 10 trays each having a depth of 1 m and a width of 50 cm. The trays were arranged in two rows next to one another and equidistant one on top of the other. The trays consisted of a perforated metal sheet having a hole diameter of 3 mm. The tray cart was pushed into a tray furnace (internal dimensions: height×width×depth: 1.30 m×1.18 m×1.10 m) which was operated with an air circulation of about 2 500 m$^3$/h. The process gas was electrically heated; the temperature was regulated by means of a thermocouple in the g as stream. The product temperature was monitored by means of 20 thermocouples which were mounted in the middle of the trays in the middle of the product b ed. The moldings were calcined in this way in a gas atmosphere comprising 1.5% by volume Of $O_2$ and 7% by volume of $NH_3$, the remainder being $N_2$, as follows:

The temperature of the gas mixture flowing through the tray furnace was increased from room temperature to 325° C. at a rate of 5° C. per minute in corresponding heating zones of the tray furnace and this temperature was maintained for 11 hours. The $NH_3$ content of the gas atmosphere was then reduced to 0%. The temperature was then increased in a corresponding manner at a rate of 2.5° C./min to 400° C. and this temperature was maintained for 80 minutes. Cooling to room temperature was subsequently effected.

The calcined extrudates thus obtained were milled in a mill (Biplex mill BQ 500) to give two-phase multimetal oxide active material powder having a mean particle diameter of from 3 to 5 μm.

d) Catalyst Preparation 70 kg of steatite rings (external diameter×height×internal diameter=7 mm×3 mm×4 mm) were initially taken as catalyst supports in a coating drum and were coated with multimetal oxide active material powder as follows:

By means of a metering chute, a total of 18.1 kg of multimetal oxide active material powder was introduced into the coating drum. At the same time, a glycerol/water mixture (glycerol:water weight ratio=1:3) in a total amount of 3.5 l was metered in as adhesion-promoting liquid.

Finally, drying was carried out in the coating drum. The proportion of active material in the coated catalysts thus produced (fixed-bed catalyst 2) was about 20% of their weight.

3) Gas-phase Catalytic Oxidation of Propene to Acrylic Acid a) The First Reaction Stage A first reaction tube (V2A stainless steel; 30 mm external diameter; 2 mm wall thickness; 26 mm internal diameter, length: 400 cm, and having a thermal tube (4 mm external diameter) centered in the middle of the reaction tube and intended for holding a thermocouple by means of which the temperature in the reaction tube can be determined) is loaded from bottom to top, on a catalyst support ledge (0.2 cm length), first with steatite rings (3 mm length, 5 mm external diameter, 1.5 mm wall thickness) having a rough surface, over a length of 90 cm, as the inert material for heating the reaction gas starting mixture, and then with a mixture of 30% by weight of the abovementioned steatite rings and 70% by weight of the fixed-bed catalyst 1, over a length of 100 cm and then only with fixed-bed catalyst 1 over a length of 200 cm, before the loading is completed with the abovementioned steatite rings over a length of 10 cm.

In the direction of flow of the reaction gas mixture (the reaction gas mixture enters at the tube end present at the catalyst support ledge), the first reaction tube is first thermostated over a length of 190 cm with a salt bath A and then over a length of 210 cm with a salt bath B (each of the two salt baths is circulated by means of a separate pump). Salt bath A defines a reaction zone A and salt bath B defines a reaction zone B.

b) The Second Reaction Stage

A second reaction tube (V2A stainless steel; 30 mm external diameter; 2 mm wall thickness; 26 mm internal diameter, length: 400 cm, and having a thermal tube (4 mm external diameter) centered in the middle of the reaction tube and intended for holding a thermocouple by means of which the temperature in the reaction tube can be determined) is connected via a 5 cm long tube adaptor (V2A stainless steel, 115 mm external diameter, 26 mm internal diameter) to the first reaction tube at the end opposite the catalyst support ledge.

The tube adaptor (it is used for sampling) and the second reaction tube connected to it are first loaded with hollow steatite cylinders (3 mm length; 7 mm external diameter, 1.5 mm wall thickness) having a rough surface, over a total length of 95 cm, for heating the acrolein-containing reaction gas mixture leaving the first reaction tube, and with a mixture of 20% by weight of the abovementioned steatite rings and 80% by weight of the fixed-bed catalyst 2, over a length of 100 cm, and then only with fixed-bed catalyst 2 over a length of 200 cm, before the loading is completed with the abovementioned steatite rings as a downstream bed over a length of 10 cm.

In the direction of flow of the reaction mixture, the second reaction tube is first thermostated over a length of 190 cm with a salt bath D and then over a length of 210 cm with a salt bath E (each of the two salt baths is circulated by means of a separate pump). Salt bath D defines a reaction zone D and salt bath E defines a reaction zone E. The salt bath does not flow round the 5 cm long tube adaptor but such tube adaptor is merely insulated by means of mineral wool in a layer thickness of 5 cm.

c) The Gas-Phase Oxidation

The first reaction tube described above is fed continuously with a reaction gas starting mixture having the following composition:

from 6.5 to 7.0% by volume of propene,
from 2.0 to 2.5% by volume of $H_2O$,
from 13.0 to 13.5% by volume of $O_2$,
from 27 bis 28% by volume of propane and
molecular oxygen as the remaining amount to 100%.

A small sample of the product gas mixture of the first reaction stage is taken via the tube adaptor for gas chromatographic analysis. Otherwise, the product gas mixture is fed directly into the downstream acrolein oxidation stage (to acrylic acid) (reaction stage 2). A small sample of the product gas mixture of the acrolein oxidation stage is likewise taken for gas chromatographic analysis.

Furthermore, the pressure difference Δp between entry into the second reaction tube and exit from the second reaction tube is measured as a function of time.

The propene space velocity of the feed of the first reaction tube is chosen as 175 l (S.T.P.) of propene per l per h.

The temperatures in the reaction zones A, B, D and E are chosen so that the propene conversion (in a single reactor pass) on emergence of the gas mixture from the first reaction tube is 95 mol % and the conversion of the acrolein formed in the first reaction tube (in a single reactor pass) on emergence of the gas mixture from the second reaction tube is 99 mol %.

According to the invention, the temperature of reaction zone A is furthermore such that the propene conversion on emergence of the gas mixture from the reaction zone A is from 40 to 80 mol %.

The following is obtained as a result:
where the abovementioned conditions are realized as the comparative example under the boundary condition "temperature of the reaction zone A=temperature of the reaction zone B" and "temperature of the reaction zone D=temperature of the reaction zone E", the pressure difference Δp increases as a function of time more rapidly than if the abovementioned conditions are realized according to the invention under the boundary condition "temperature of the reaction zone A<temperature of the reaction zone B" and "temperature of the reaction zone D=temperature of the reaction zone E".

We claim:

1. A process for the catalytic gas-phase oxidation of propene to acrylic acid, in which a reaction gas starting mixture which comprises propene, molecular oxygen and at least one inert gas and contains the molecular oxygen and the propene in a molar $O_2$: $C_3H_6$ ratio of $\geq 1$ is passed, in a first reaction stage, using a propene loading of $\geq 160$ liter (S.T.P.) of propene/liter of fixed catalyst bed 1 per hour, under formation of acrolein and optionally acrylic acid as a byproduct, over a fixed catalyst bed 1 which is arranged in two spatially successive reaction zones A, B, the temperature of the reaction zone A being from 300 to 370° C. and the temperature of the reaction zone B beings from 305 to 380° C. and simultaneously at least 5° C. above the temperature of the reaction zone A wherein catalyst bed 1 comprises on active material catalyst bed 1 being at least one multimetal oxide containing at least the elements Mo, Fe and Bi, in such a way that the propene conversion in reaction zone A is from 40 to 80 mol % and the propene conversion during a single pass through the fixed catalyst bed 1 is $\geq 90$ mol % and the associated selectivity of the acrolein formation and of the acrylic acid byproduct formation together are $\geq 90$ mol %, and the resulting product gas mixture, which contains the molecular oxygen and the acrolein in a molar $O_2$: $C_3H_4O$ ratio of $\geq 0.5$, is passed, in a second reaction stage, over a fixed catalyst bed 2 which is arranged either in a single reaction zone C or in two spatially successive reaction zones D, E, the temperature of the reaction zone C being from 230 to 300° C. and the temperature of the reaction zone D being from 230 to 280° C. and the temperature of the reaction zone E being from 250 to 300° C. and simultaneously at least 5° C. above the temperature of the reaction zone D and the active material of catalyst bed 2 being at least one multimetal oxide containing at least the elements Mo and V, in such a way that the acrolein conversion during a single pass through the reaction zone C or the reaction zones D and E is $\geq 90$ mol % and the selectivity of the acrylic acid formation balanced over all reaction zones and based on propene converted is $\geq 80$ mol %, the sequence in which the reaction gas starting mixture flows through the reaction zones corresponding to the alphabetic sequence of the reaction zones, wherein both the fixed catalyst beds 1 and 2 and the reaction zones A, B and C or A, B, D and E are present in a single tube-bundle reactor comprising a plurality of catalyst tubes.

2. A process as claimed in claim 1, wherein the propene conversion in reaction zone A is from 50 to 70 mol %.

3. A process as claimed in claim 1, wherein the propene conversion in reaction zone A is from 65 to 75 mol %.

4. A process as claimed in claim 1, wherein the temperature of the reaction zone B is at least 10° C. above the temperature of the reaction zone A.

5. A process as claimed in claim 1, wherein the propene loading of the fixed catalyst bed 1 is $\geq 180$ liter (S.T.P.)/ 1·hour.

6. A process as claimed in claim 1, wherein the active material of the fixed catalyst bed is at least one multimetal oxide of the formula I

$$Mo_{12}Bi_aFe_bX^1_cX^2_dX^3_eX^4_fO_n \qquad (I),$$

where
$X^1$ is at least one of nickel or cobalt,
$X^2$ is at least one of thallium, an alkali metal or an alkaline earth metal,
$X^3$ is at least one of zinc, phosphorus, arsenic, boron, antimony, tin, cerium, lead or tungsten, X⁴ is at least one of silicon, aluminum, titanium or zirconium, a is from 0.5 to 5, b is from 0.01 to 5, c is from 0 to 10, d is from 0 to 2, e is from 0 to 8, f is from 0 to 10 and n is a number which is determined by the valency and frequency of the elements other than oxygen in formula I.

7. A process as claimed in claim 1, wherein the temperature of the reaction zone E is at least 20° C. above the temperature of the reaction zone D.

8. A process as claimed in claim 1, wherein the selectivity of the acrylic acid formation, balanced over both reaction stages and based on propene converted is $\geq 90$ mol %.

9. A process as claimed in claim 1, wherein the active material of the fixed catalyst bed 2 is at least one multimetal oxide of the formula IV

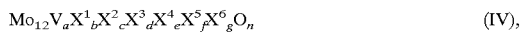

$$Mo_{12}V_aX^1_bX^2_cX^3_dX^4_eX^5_fX^6_gO_n \quad (IV),$$

where

X¹ is at least one of W, Nb, Ta, Cr or Ce,

X² is at least one of Cu, Ni, Co, Fe, Mn or Zn,

X³ is at least one of Sb or Bi,

X⁴ is one or more alkali metals,

X⁵ is one or more alkaline earth metals,

X⁶ is at least one of Si, Al, Ti-or Zr, a is from 1 to 6, b is from 0.2 to 4, c is from 0.5 to 18, d is from 0 to 40, e is from 0 to 2, f is from 0 to 4, g is from 0 to 40 and n is a number which is determined by the valency and frequency of the elements other than oxygen in formula IV.

10. In a method of producing a polymer comprising acrylic acid, the improvement comprising preparing acrylic acid according to the process of claim 1.

11. In a method of producing a polymer comprising acrylic acid, the improvement comprising preparing acrylic acid according to the process of claim 2.

12. In a method of producing a polymer comprising acrylic acid, the improvement comprising preparing acrylic acid according to the process of claim 3.

13. In a method of producing a polymer comprising acrylic acid, the improvement comprising preparing acrylic acid according to the process of claim 4.

14. In a method of producing a polymer comprising acrylic acid, the improvement comprising preparing acrylic acid according to the process of claim 5.

15. In a method of producing a polymer comprising acrylic acid, the improvement comprising preparing acrylic acid according to the process of claim 6.

16. In a method of producing a polymer comprising acrylic acid, the improvement comprising preparing acrylic acid according to the process of claim 7.

17. In a method of producing a polymer comprising acrylic acid, the improvement comprising preparing acrylic acid according to the process of claim 8.

18. In a method of producing a polymer comprising acrylic acid, the improvement comprising preparing acrylic acid according to the process of claim 9.

* * * * *